(12) United States Patent
Paul et al.

(10) Patent No.: US 8,388,549 B2
(45) Date of Patent: Mar. 5, 2013

(54) ANATOMICAL THERMAL SENSING DEVICE AND METHOD

(75) Inventors: Saurav Paul, Minneapolis, MN (US); Todd Stangenes, Minneapolis, MN (US); Riki Thao, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 342 days.

(21) Appl. No.: 12/751,946

(22) Filed: Mar. 31, 2010

(65) Prior Publication Data
US 2010/0191142 A1 Jul. 29, 2010

Related U.S. Application Data

(63) Continuation-in-part of application No. 12/345,243, filed on Dec. 29, 2008.

(51) Int. Cl.
*A61B 5/00* (2006.01)
(52) U.S. Cl. ......................... 600/549
(58) Field of Classification Search ............ 600/587, 600/549, 547; 606/20, 27, 32, 108, 170, 606/195, 167, 164, 113
See application file for complete search history.

(56) References Cited

U.S. PATENT DOCUMENTS

| | | | |
|---|---|---|---|
| 5,427,119 A | 6/1995 | Swartz et al. | |
| 5,628,316 A | 5/1997 | Swartz et al. | |
| 5,690,611 A | 11/1997 | Swartz et al. | |
| 5,725,512 A | 3/1998 | Swartz et al. | |
| 5,800,413 A | 9/1998 | Swartz et al. | |
| 5,814,028 A | 9/1998 | Swartz et al. | |
| 5,814,029 A | 9/1998 | Hassett | |
| 5,833,673 A | 11/1998 | Ockuly et al. | |
| 5,840,027 A | 11/1998 | Swartz et al. | |
| 5,846,223 A | 12/1998 | Swartz et al. | |
| 5,879,296 A | 3/1999 | Ockuly et al. | |
| 6,090,084 A | 7/2000 | Hassett et al. | |
| 6,156,018 A | 12/2000 | Hassett | |
| 6,200,315 B1 | 3/2001 | Gaiser et al. | |
| 6,203,531 B1 | 3/2001 | Ockuly et al. | |
| 6,526,302 B2 | 2/2003 | Hassett | |
| 6,752,804 B2 | 6/2004 | Simpson et al. | |
| 7,008,381 B2 | 3/2006 | Janssens | |
| 7,276,064 B2 | 10/2007 | Paul | |
| 2001/0056232 A1 | 12/2001 | Lardo et al. | |

(Continued)

FOREIGN PATENT DOCUMENTS
WO WO-2004026134 4/2004

OTHER PUBLICATIONS

Burnett, J. M. et al., "Intracardiac echocardiography 101: The beginner's guide to ICE imaging and cardiac structure recognition", May 2005.

(Continued)

*Primary Examiner* — Brian Szmal
(74) *Attorney, Agent, or Firm* — Dykema Gossett PLLC

(57) ABSTRACT

A medical device utilizing temperature sensing to identify or assess anatomical bodies or structures includes an elongate tubular member, at least one electrode, a thermal sensor, and a temperature response assessment system or component. The at least one electrode may be connected to the distal portion of the elongate tubular member, and the one or more electrode can be configured to provide energy or heat to a portion of an anatomical body or structure. The thermal sensor may be configured to measure the thermal response of the portion of an anatomical body or structure, e.g., tissue or blood pools. The temperature response assessment system or component can be coupled to the thermal sensor. In embodiments, the device may include a lumen and port opening, which may accommodate a tool, such as a needle. Methods for using temperature sensing to identify an anatomical body or structure are also disclosed.

20 Claims, 6 Drawing Sheets

U.S. PATENT DOCUMENTS

| | | |
|---|---|---|
| 2002/0169377 A1 | 11/2002 | Khairkhahan et al. |
| 2003/0144657 A1 | 7/2003 | Bowe et al. |
| 2003/0181942 A1 | 9/2003 | Sutton et al. |
| 2004/0133113 A1 | 7/2004 | Krishnan |
| 2005/0101984 A1 | 5/2005 | Chanduszko et al. |
| 2005/0149097 A1 | 7/2005 | Regnell et al. |
| 2005/0177182 A1 | 8/2005 | Van der Burg et al. |
| 2006/0009715 A1 | 1/2006 | Khairkhahan et al. |
| 2006/0009737 A1 | 1/2006 | Whiting et al. |
| 2006/0064062 A1 | 3/2006 | Gurusamy et al. |
| 2006/0095052 A1 | 5/2006 | Chambers et al. |
| 2006/0276710 A1 | 12/2006 | Krishnan |
| 2006/0276749 A1 | 12/2006 | Selmon et al. |
| 2007/0270741 A1 | 11/2007 | Hassett et al. |
| 2007/0270751 A1 | 11/2007 | Stangenes et al. |
| 2008/0103400 A1 | 5/2008 | Krishnan |

OTHER PUBLICATIONS

Daoud, Emile G. et al., "Intracardiac echocardiography to guide transseptal left heart catheterization for radiofrequency catheter ablation", 2007.

Hanaoka, Takeshi et al., "Shifting of puncture site in the fossa ovalis during radiofrequency catheter ablation", 2003.

Liang, K et al., "Intra-cardiac echocardiography guided trans-septal puncture in patients with dilated left atrium undergoing percutaneous transvenous mitral commissurotomy", 2003.

Sosa, Eduardo et al., "Epicardial mapping and ablation techniques to control ventricular tachycardia"; Apr. 2005.

Szili-Torok, T et al., "Transseptal left heart catheterisation guided by intracardiac echocardiography", 2001.

ANATOMICAL THERMAL SENSING DEVICE AND METHOD

CROSS-REFERENCE TO RELATED APPLICATIONS

This application is a continuation-in-part of U.S. appplication Ser. No. 12/345,243, filed 29 Dec. 2008, now pending, which is hereby incorporated by reference in its entirety as though fully set forth herein.

BACKGROUND OF THE INVENTION a. Field of the Invention

The instant invention relates generally to anatomical devices and methods, including devices and methods useful for determining or locating relative positions within different parts of a varying anatomical structure (e.g., having different thermal capacity, tissue thickness, electrical or blood flow characteristics and the like).

b. Background Art

Practices are known for locating and gaining access to anatomical structures, including structures provided within a human body. For example, a current practice for gaining access to the left atrium is to manually puncture the intra-atrial septum at the location of the fossa ovalis. Because the location is difficult to find, and failure to puncture in a proper location can lead to significant complications, a physician may employ a combination of techniques to help verify that an appropriate site has been identified. Such techniques may include, inter alia, fluoroscopy, pressure monitoring, contrast injection, or various combinations of the foregoing.

Among other things, the teachings of the present disclosure provide a device and technique, whether employed alone or in combination with other techniques, to verify appropriate positions or locations within an anatomical body or structure.

BRIEF SUMMARY OF THE INVENTION

Medical devices that utilize temperature sensing to identify or assess anatomical bodies or structures are disclosed. Embodiments of the devices include an elongate tubular member, at least one electrode, a thermal sensor, and a temperature response assessment system or component. The elongate tubular member includes a distal portion having a distal tip and a side wall. The at least one electrode may be connected to the distal portion of the elongate tubular member, and the one or more electrode can be configured to provide energy to a portion of an anatomical body or structure. The thermal sensor may be configured to measure the thermal response of the portion of an anatomical body or structure, which may include, for example and without limitation, tissue or blood pools from the application and subsequent cessation or substantial cessation of sub-threshold energy. The temperature response assessment system or component can be operatively coupled to the thermal sensor.

In embodiments, the device may include a lumen and port opening, which may, for example, accommodate a tool, e.g., an access tool, such as a needle. Methods for using temperature sensing to identify an anatomical body or structure are also disclosed.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
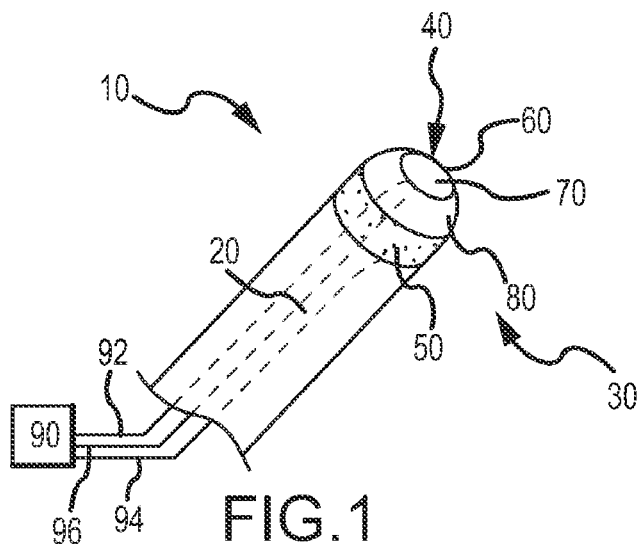
FIG. 1 illustrates a distal portion of a device in accordance with an embodiment.

A device 10 according to an embodiment is generally shown in FIG. 1. The device 10 includes an elongate tubular member 20 and a distal portion 30. The distal portion 30 may include a thermal sensor or sensing mechanism that can be used for identifying or locating anatomical bodies or structures based upon relative thermal absorptive and dissipative properties of different portions of said bodies or structures. In embodiments, a device 10 may be configured to locate an anatomical landmark, such as portions of body tissue having such different characteristics. For example, in an application a device 10 may be employed to locate particular portions of a heart, including the fossa ovalis, relative to other portions of the heart.

With further reference to FIG. 1, the illustrated device 10 may include a first electrode 40 and a second electrode 50. The first electrode 40 can be located at the distal tip 60 of the distal portion 30, and the second electrode 50 may be provided spaced proximally of the first electrode 40. The first electrode 40 may be a button-type, or a discrete unitary electrode and the second electrode 50 may be a ring electrode. For some embodiments the electrodes may, if desired, be comprised of nonconductive polymers doped or containing conductive material(s) such as flakes or particles of gold or the like, and thus may be MRI compatible.

The first electrode may include a thermal sensor 70. In embodiments, the thermal (or temperature) sensor 70 may, for example, be a thermocouple, thermistor, an optical thermal sensor, or other type of temperature-monitoring sensor known in the art. The thermal sensor can be configured to, inter alia, provide feedback for the assessment of a thermal response gradient. In embodiments, the thermal sensor may be insulated or spaced from the electrode and may have a rapid time constant and high Q value. If the thermal sensor(s) is embedded in an electrode (the electrode serves as a heat transfer mechanism) a latency can be expected (and may be compensated for in an associated thermal response assessment). Moreover, for some embodiments, the sensor may, in addition to providing temperature sensing, may be configured to measure impedance. Also, as generally illustrated in FIG. 1, a segment or region 80 may be provided between a first electrode 40 and second electrode 50. For some embodiments the segment or region 80 may provide a gap between the electrodes that is thermally conductive, but electrically insulative. The segment or region 80 may, for example and without limitation, comprise a non-conductive polymer. Moreover, in alternate embodiments, the thermal sensor 70 may be provided at other locations and may, for example, be located adjacent to the first electrode 40.

In embodiments, at least one electrode may be configured to provide energy to a portion of an anatomical structure, e.g., a tissue portion, in a so-called unipolar or a bipolar configuration. Herein, a single electrode coupled to a portion of a medical device such as a catheter or introducer with a return path to another electrode not disposed on the device is deemed a unipolar configuration while a pair of spaced apart electrodes on the device is deemed bipolar. Thus the energy, which may be in the form of heat, may, without limitation, be applied by one or more electrodes employing unipolar or bipolar techniques, and the energy conveyed may, for example, be in the form of radio frequency (RF), microwave, laser, ultrasound, or closed-loop circulated heated fluids. It is noted that the energy or heat that is transferred by the device 10 may be in the form of a non-ablating amount or level of energy or heat that is delivered over a period of time. That is, embodiments of the disclosure may employ a "sub-threshold" energy such that the energy that is applied will not damage, ablate or otherwise promote necrosis or tend to perforate the tissue to which the energy is applied.

Without limitation, when first and second electrodes 40, 50 are provided, the electrodes may be configured to create a bi-pole along the distal portion 30 of the device 10. When RF energy is delivered between the poles, an adjacent anatomical structure (e.g., adjacent tissue) will be heated. The thermal sensor 70 can be configured to measure the thermal response of the anatomical structure.

A controller 90, which may include a temperature response assessment system or component, may be operatively coupled to the thermal sensor 70 and/or one or more electrodes associated with the device 10. In embodiments, the temperature response assessment system or component may be integrated within a controller that may further be configured to control the energy or heat provided by one or more electrodes, whether the electrodes are separately controlled or controlled in combination. For example, without limitation, in FIG. 1, the controller 90 is generically shown linked by wires or conduits 92, 94 to the first and second electrodes 40, 50, respectively. Further, as illustrated, a separate wire or conduit 96 may couple the controller 90 and thermal sensor. The controller may be configured to constrain the amount(s) or timing (and duration) of energy or heat provided by the device vis-à-vis one or more electrodes associated with the device. In embodiments, the controller may be configured to, inter alia: (a) constrain or "cap" the amount of the energy or heat provided by one or more electrodes—whether at any point in time and/or within a predetermined or specified period of time; (b) provide forms of temporal limitation(s) for the device, and the device may include a form of timing mechanism (e.g., a timer or clock) that assists with controlling the provision of energy or heat by the electrode or electrodes; (c) provide a specified range or profile of energy or heat that the device will be configured to observe; (d) include predetermined or specified not-to-exceed or "cut-off" temperature values (e.g., for tissue portions or anatomical structures) that may not be exceeded (i.e., the device will cease to supply (or reduce) heat or energy); (e) include algorithmic control(s) (such as permitting the picking of a set point temperature and measuring the time to reach the setpoint with limits based on time or energy delivered and/or a time rate-of-change metric for energy, temperature or other measurand); and include manual controls, which without limitation, may permit manual setting of the amount(s) of heat or energy applied, the duration(s), or both the amount(s) and durations (e.g., in algorithmic profiles).

The disclosed concept recognizes and utilizes the finding that different anatomical structures or bodies can be assessed as exhibiting differing rates of temperature increase or decrease. By way of example, device 10 may be configured to locate anatomical structures, such as the fossa ovalis. More specifically, the inventors hereof have found that the interatrial septum exhibits a characteristic rate of temperature increase during application of energy and rate of temperature decrease (following cessation or substantial reduction of energy application) based on naturally occurring cooling effects associated with adjacent blood flow. That is, in the case of the interatrial septum, blood flow within the left atrium will have a greater impact on the thermal response in areas where the tissue is comparatively thin. Because the fossa ovalis is the thinnest portion of the septal wall, with the relevant blood flow, the fossa ovalis encounters notably different thermal effects, including heat transfer effects, compared to other portions of the interatrial septum. Thus, by monitoring the rates of temperature increase and/or decrease with respect to portions of the interatrial septum, embodiments of device 10 can permit a user to locate the fossa ovalis with a high degree of certainty.

Figure 2:
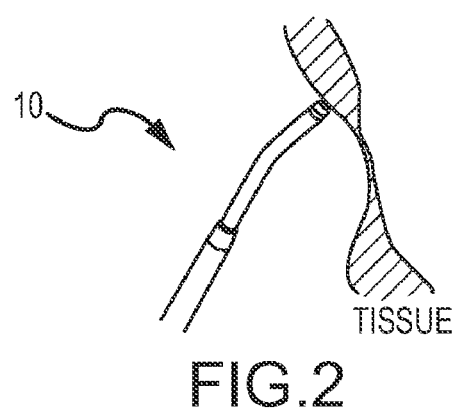
FIG. 2 illustrates an embodiment of a device in contact with a relatively thicker portion of tissue.
Figure 3:
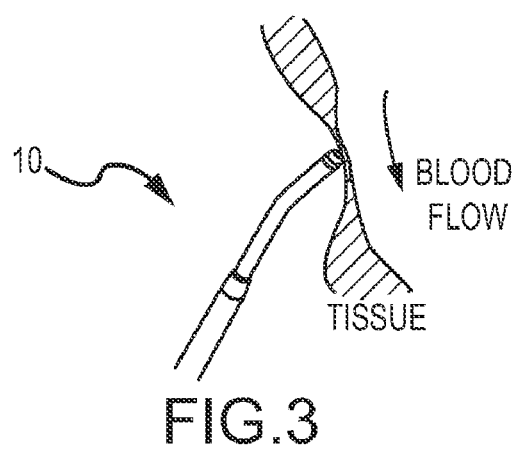
FIG. 3 illustrates an embodiment of a device similar to that depicted in FIG. 2, depicted in contact with a relatively thin portion of tissue.

FIGS. 2 and 3 provide a representative example of how a device 10 may be used to locate an appropriate site of puncture (e.g., the fossa ovalis) based on tissue thickness. FIG. 2 illustrates device 10 in contact with a thick portion of tissue in the septum. The device 10 may be used to determine or observe a first thermal response—e.g., following cessation (or substantial reduction) of energy application associated with the thick portion of tissue. With regard to the notion of a substantial reduction in energy applied to tissue, the inventors suggest that without undue experimentation those of skill in the art will appreciate that it could be as little as one-half or less of a reduction for certain tissue substrates. FIG. 3 illustrates the device 10 in contact with a relatively thin portion of tissue. The thermal response of the relatively thinner portion of tissue is relatively fast when compared with the first thermal response associated with the thicker portion of tissue.

Figure 4A:
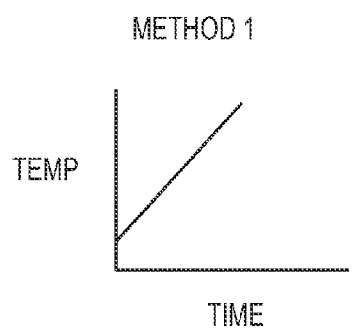
FIG. 4A depicts a representative "heating" profile associated with the treated tissue portion illustrated in FIG. 2.
Figure 4B:
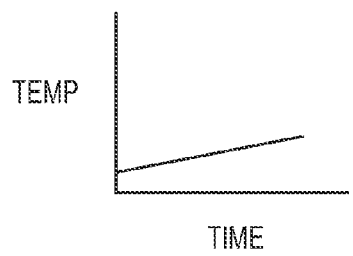
FIG. 4B depicts a representative "heating" profile associated with the tissue portion illustrated in FIG. 3.

It is noted that the thermal response of the relevant tissue may be observed in the form of a total (e.g., overall) temperature increase or decrease, a rate-of-change temperature increase or decrease, and/or a time-to-reach a preset temperature (e.g., time from a first measured temperature to a desired maximum or an intermediate temperature below a maximum or other preset temperature), as well as variations and combinations of the foregoing. FIGS. 4A and 4B generally illustrate thermal profiles during energy application. FIG. 4A depicts a representative "heating" profile associated with the treated tissue portion (i.e., the relatively thicker portion) illustrated in FIG. 2. Similarly, FIG. 4B depicts a heating profile associated with the treated tissue portion (i.e., the comparatively thinner portion) illustrated in FIG. 3. In the second profile—shown in FIG. 4B—the tissue temperature rises more slowly and provides a measurable distinguishing characteristic for the comparative tissue portions.

Figure 5A:
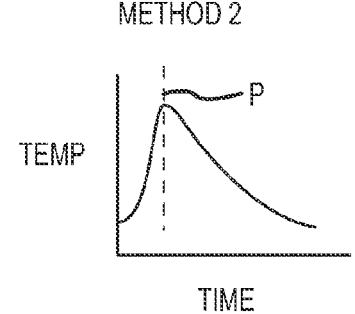
FIG. 5A depicts a representative "heating-cooling" profile associated with the treated tissue portion illustrated in FIG. 2.
Figure 5B:
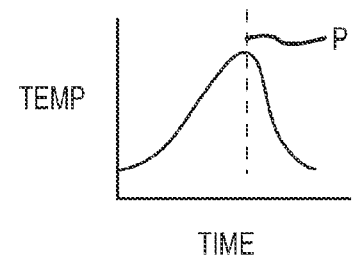
FIG. 5B depicts a representative "heating-cooling" profile associated with the treated tissue portion illustrated in FIG. 3.

FIGS. 5A and 5B generally illustrate thermal response profiles—e.g., following a cessation of energy application. FIG. 5A depicts a representative "heating-cooling" response profile associated with the treated tissue portion (i.e., the relatively thicker portion) illustrated in FIG. 2. Similarly, FIG. 5B depicts a heating-cooling response profile associated with the treated tissue portion (i.e., the comparatively thinner portion) illustrated in FIG. 3. In the first response profile—shown in FIG. 5A—the associated tissue is thicker and, therefore, cools comparatively more slowly than the response profile for a relatively thinner tissue portion—such as generally depicted in FIG. 5B.

Embodiments of the devices may also be used to distinguish types or conditions of tissue that may or may not be of different thicknesses. For example, scar or treated tissue is known to generally exhibit different thermal characteristics than unscarred or untreated tissue. That is, their temperature response profiles differ and can be detected and distinguished.

Figure 6:
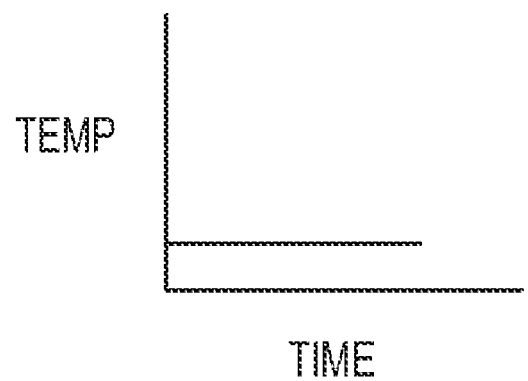
FIG. 6 illustrates a representative "heating" profile when the device is positioned in a blood pool.
Figure 7:
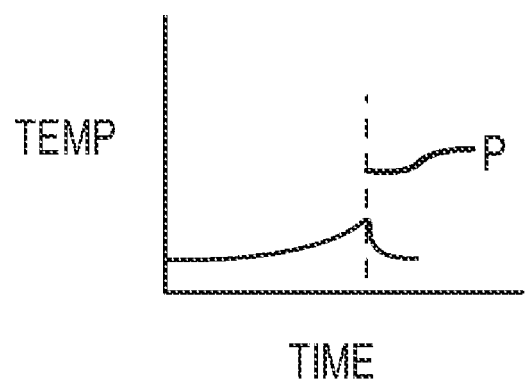
FIG. 7 illustrates a representative "heating-cooling" profile when the device is positioned in a blood pool.

Moreover, embodiments of the device may also be used to determine whether the distal end (e.g., distal tip) of the device is in contact with tissue. FIG. 6 illustrates a representative "heating" profile (e.g., as depicted with FIGS. 4A and 4b) when the distal tip is not in contact with tissue, but instead is in a blood pool. The profile may be relatively flat in nature. Similarly, FIG. 7 illustrates a representative "heating-cooling" profile (e.g., as depicted with FIGS. 5A and 5b) when the distal tip is not in contact with tissue, but instead is positioned in a blood pool. It is noted that at the point in time P, where cooling generally begins after energy application stops, a very fast decline in temperature may be observed.

Figure 8:
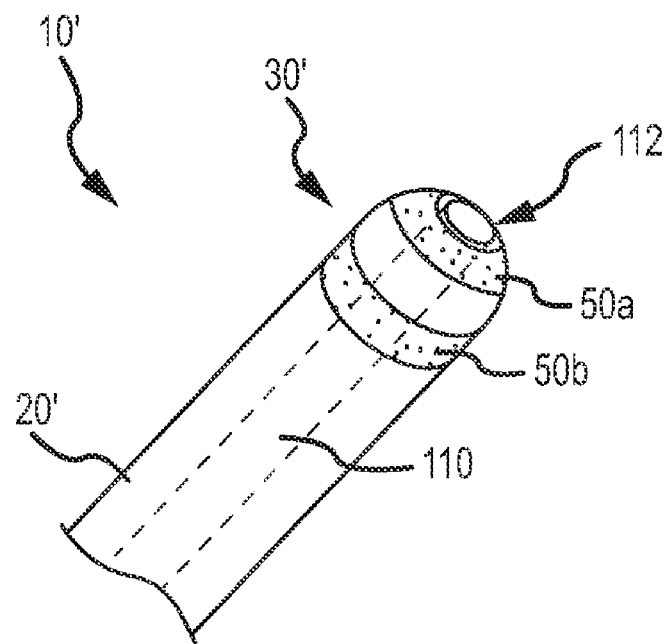
FIG. 8 illustrates an embodiment of a device including two ring electrodes and a lumen.
Figure 9:
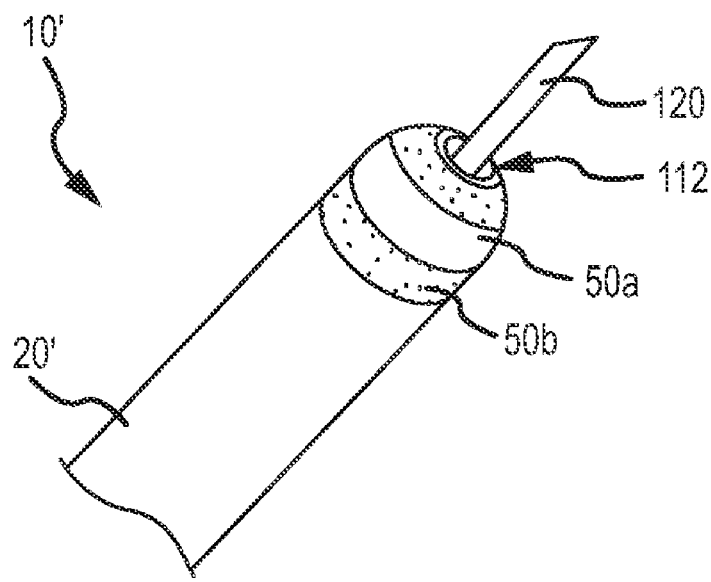
FIG. 9 illustrates the device of FIG. 8 with a needle that extends through the lumen.

FIG. 8 illustrates another embodiment of a device 10' illustrating additional aspects of the disclosure. The illustrated device 10' includes a first electrode 50a and a second electrode 50b. In an embodiment, one or both of the first electrode 50a and the second electrode 50b may include a thermal sensor. The first and second electrodes 50a and 50b—which may comprise ring electrodes—are located proximally of the distal tip of the device. The illustrated device 10' further includes a lumen 110 provided within the tubular elongate tubular member 20'. The illustrated lumen 110 may include a lumen opening 112, which in this embodiment is shown at the distal tip of the distal end 30' of the device 10'. In embodiments, the lumen 110 may be a fluid and/or a needle lumen. It is noted that with irrigated embodiments, the thermal sensor may be disposed out of the direct flow of any associated irrigation fluid. FIG. 9 depicts the device 10' of FIG. 8 with a tool, such as a needle 120 that extends through the lumen 110, and may extend through the lumen opening 112. The needle 120 may, for example, be a flexible non-conductive needle and/or may be used to puncture tissue, such as that associated with the intra-atrial septum. With embodiments of devices that include a lumen, it may be advantageous to provide an electrode (or a plurality of electrodes or electrode segments) in close proximity to the lumen opening.

Figure 10:
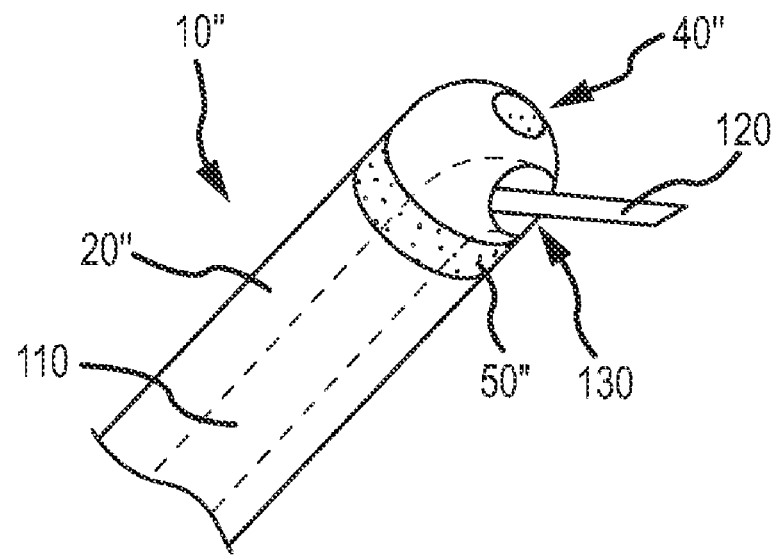
FIG. 10 illustrates an embodiment of a device including a side port opening provided between a first electrode and a second electrode.
Figure 11:
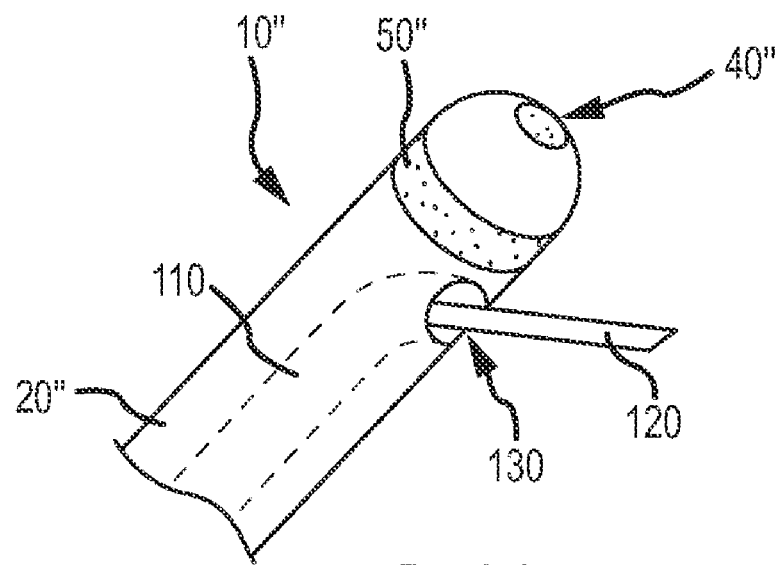
FIG. 11 illustrates an embodiment of a device including a side port opening provided proximally of a first electrode and a second electrode.

FIG. 10 illustrates another embodiment of a device 10" that includes a side port opening 130 in the elongate tubular member 20". In the illustrated embodiment the side port opening 130 is provided between a first electrode 40" and a second electrode 50". The first electrode 40" may include a thermal sensor, and the device 10" additionally includes a lumen 110 provided within the tubular elongate tubular member 20". As generally shown, a needle 120 may extend through the lumen 110 and can extend externally through the side port opening 130. FIG. 11 illustrates an embodiment of a device similar to that shown in FIG. 10; however, a side port opening 130 is provided proximally of a first electrode 40" and a second electrode 50".

Figure 12:
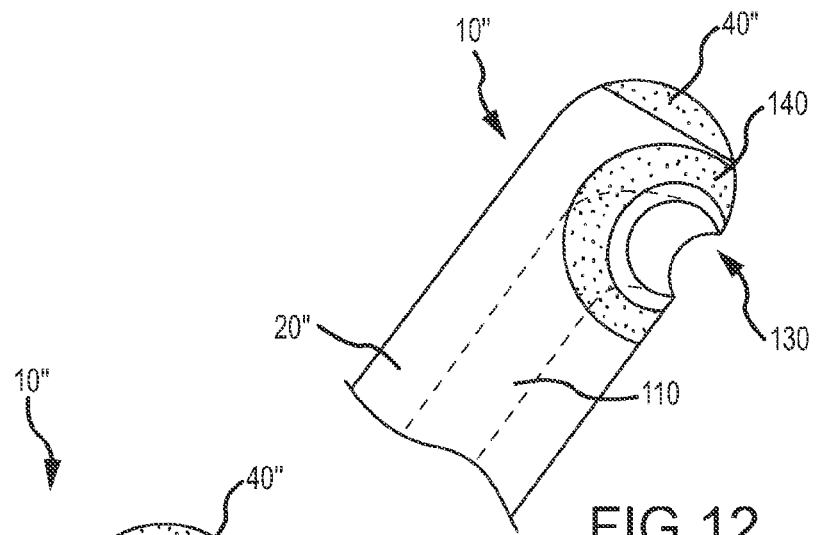
FIG. 12 illustrates an embodiment of a device including an electrode ring that encircles or substantially circumscribes a side port opening.
Figure 13:
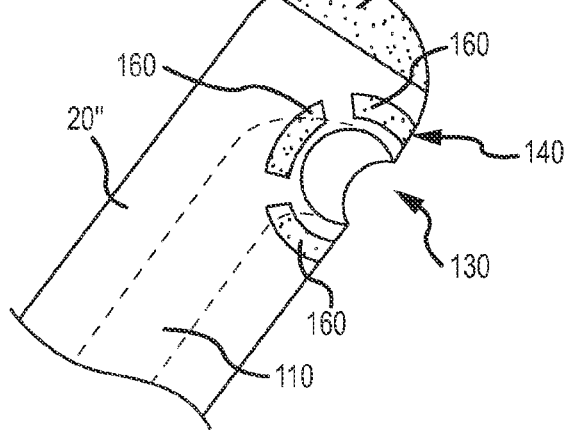
FIG. 13 illustrates an embodiment of a device of the type shown in FIG. 12, including a segmented electrode ring that substantially encircles a side port opening.
Figure 14:
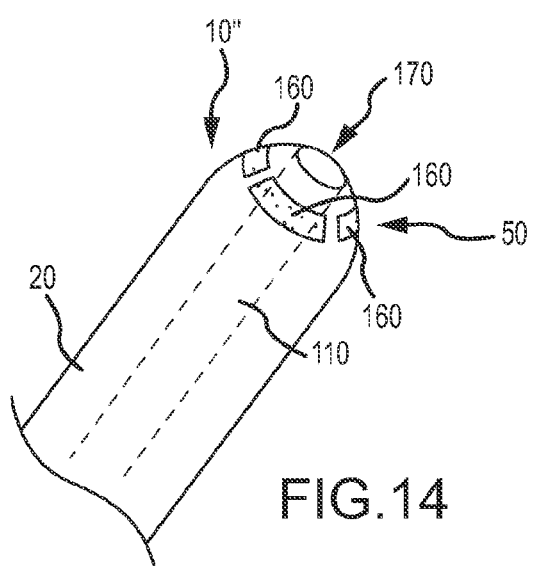
FIG. 14 illustrates an embodiment of a device similar to that shown in FIG. 8, the device including a lumen and a segmented electrode ring that substantially encircles the lumen.

Further embodiments of devices 10" that include side port openings 130 are shown in FIGS. 12-14. FIG. 12 generally illustrates an electrode ring 140 that encircles or substantially circumscribes the side port opening 130. As illustrated, the electrode ring 140 may be slightly offset, i.e., radially spaced from, the periphery of the side port opening 130. FIG. 13 illustrates an embodiment of a device 10" similar to that shown in FIG. 12; however, the electrode ring 140 is comprised of a plurality of spaced, segmented electrodes 160. As generally shown in the illustrated embodiment, the segmented electrodes 160 may be configured to comprise a non-continuous ring that substantially encircles the associated side port opening 130. Additionally, as generally illustrated in FIGS. 12 and 13, the device 10" may optionally include a first/distal tip electrode 40"'. The first, tip electrode 40" is not limited to the form illustrated, and may be provided in other configurations. Further, if included, the first/distal tip electrode 40" may be configured for bi-polar sensing and/or may include an integrated thermal sensor.

FIG. 14 illustrates an embodiment of a device 10" similar to that shown in FIG. 8 including a lumen 110 and a segmented electrode ring 50 that substantially encircles a distal tip port opening 170 (which may be similar to lumen opening 112, previously described). The device 10" shown in FIG. 14 may also include thermal sensor provided in connection with the electrode ring 50 and which may be located at or about the distal tip port opening 170. The segmented electrode ring 50 may include a plurality of spaced, segmented electrodes 160, and may comprise a non-continuous ring.

Devices in accordance with embodiments of the disclosure may further be adapted for or used in connection with various navigation and/or visualization systems. That is, if desired for some applications, one or more systems may be employed to further confirm that a desired or specified anatomical landmark has been located by devices provided in accordance with teachings of the present disclosure. By way of example, and without limitation, such visualization systems may include fluoroscopic type systems; impedance-type systems (such as EnSite NAVX™ commercially available from St. Jude Medical, Inc.); magnetic visualization and position and orientation systems; MRI-based systems. It is noted that the electrode(s) employed by the device may be adapted to coordinate with one or more visualization systems. By way of example, without limitation, if a magnetic-type visualization system (e.g., gMPS commercialized by MediGuide, Ltd. or the CARTO system from Biosense Webster, Inc., a Johnson & Johnson company) is intended to be used in connection with a device of the type associated with this disclosure, the device may be configured to include additional/necessary elements, such as magnets or coils.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A temperature sensing medical device, the device comprising:
    an elongate tubular member including a distal portion having a distal tip and a side wall;
    at least one electrode connected to the distal portion of the elongate tubular member, the electrode configured to apply a sub-threshold amount of energy to a portion of an anatomical body or structure; and
    a thermal sensor configured to measure a thermal response of the portion of an anatomical body or structure in response to the application of the sub-threshold amount of energy to the portion of the anatomical body or structure and provide an output signal related thereto; and
    a temperature response assessment system or component operatively coupled to receive the output signal from the thermal sensor and to characterize the anatomical body or structure based upon at least one of a thermal absorptive property and a thermal dissipative property of the portion of an anatomical body or structure.

2. The device of claim 1, wherein the at least one electrode comprises a first electrode and a second electrode.

3. The device of claim 2, wherein the first electrode comprises an electrode located at the distal tip of the elongate tubular member and the second electrode comprises an electrode located along the distal portion of the elongate tubular member proximally of the first electrode.

4. The device of claim 3, wherein the first electrode comprises a button electrode, and the second electrode comprises a ring electrode.

5. The device of claim 3, wherein the first electrode and the second electrode provide a bi-pole along the distal portion of the elongate tubular member.

6. The device of claim 5, wherein the energy comprises a radio frequency (RF) energy, and the RF energy is delivered in a bipolar configuration between the first electrode and the second electrode.

7. The device of claim 1, wherein the energy comprises at least one of a radio frequency (RF) energy, microwave energy, laser energy, an ultrasound energy, and a closed-loop circulation of a comparatively warmer fluid.

8. The device of claim 1, wherein the device includes a plurality of thermal sensors.

9. The device of claim 1, including a controller configured to control the energy provided by the at least one electrode.

10. The device of claim 9, wherein the controller is configured to constrain the amount of energy or duration of energy provided by the at least one electrode.

11. The device of claim 9, wherein the controller includes manual control.

12. The device of claim 9, wherein the controller is further configured to limit the energy to a specified range of energy or metric.

13. The device of claim 12, wherein the controller is further configured to temporally limit the application of energy.

14. The device of claim 9, wherein the controller includes algorithmic control.

15. The device of claim 10, the temperature response assessment system or component is integrated with the controller.

16. The device of claim 1, wherein the elongate tubular member includes a lumen extending therethrough in a longitudinal direction.

17. The device of claim 16, including a side port opening extending through the side wall of the elongate tubular member.

18. The device of claim 16, including a flexible puncture member, the flexible puncture member being insertable through the lumen and having a distal end.

19. The device of claim 1, wherein the device can be deflectable or pre-curved.

20. The device of claim 1, including a visualization system.

* * * * *